(12) United States Patent
Siegel

(10) Patent No.: US 10,758,265 B2
(45) Date of Patent: Sep. 1, 2020

(54) CARDIOVASCULAR ACCESS AND DEVICE DELIVERY SYSTEM

(71) Applicant: CEDARS-SINAI MEDICAL CENTER, Los Angeles, CA (US)

(72) Inventor: Robert James Siegel, Beverly Hills, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 422 days.

(21) Appl. No.: 15/525,914

(22) PCT Filed: Nov. 13, 2015

(86) PCT No.: PCT/US2015/060726
§ 371 (c)(1),
(2) Date: May 10, 2017

(87) PCT Pub. No.: WO2016/077783
PCT Pub. Date: May 19, 2016

(65) Prior Publication Data
US 2017/0325842 A1 Nov. 16, 2017

Related U.S. Application Data

(60) Provisional application No. 62/079,811, filed on Nov. 14, 2014.

(51) Int. Cl.
*A61B 17/34* (2006.01)
*A61F 2/24* (2006.01)
*A61B 17/00* (2006.01)

(52) U.S. Cl.
CPC ...... *A61B 17/3421* (2013.01); *A61B 17/0057* (2013.01); *A61B 17/00234* (2013.01);
(Continued)

(58) Field of Classification Search
CPC .......... A61B 17/00234; A61B 17/0057; A61B 2017/00243; A61B 2017/00247;
(Continued)

(56) References Cited

U.S. PATENT DOCUMENTS

| | | |
|---|---|---|
| 4,777,951 A | 10/1988 | Cribier et al. |
| 5,201,880 A | 4/1993 | Wright et al. |
| 5,573,540 A | 11/1996 | Yoon |
| 5,575,799 A | 11/1996 | Bolanos et al. |
| 5,609,598 A | 3/1997 | Laufer et al. |
| 5,626,588 A | 5/1997 | Sauer et al. |
| 5,716,367 A | 2/1998 | Koike et al. |
| 6,029,671 A | 2/2000 | Stevens et al. |
| 6,051,014 A | 4/2000 | Jang |
| 6,090,096 A | 7/2000 | St. Goar et al. |

(Continued)

FOREIGN PATENT DOCUMENTS

| | | |
|---|---|---|
| EP | 1 674 040 | 6/2006 |
| EP | 1 539 015 | 4/2011 |

(Continued)

OTHER PUBLICATIONS

Bhargava et al., "Biosense Left Ventricular Electromechanical Mapping", Asian Cardiovasc Thorac Ann 1999, 7:345-52.
(Continued)

*Primary Examiner* — Darwin P Erezo
*Assistant Examiner* — Christian D Knauss
(74) *Attorney, Agent, or Firm* — Knobbe Martens Olson & Bear LLP

(57) ABSTRACT

A system and method of accessing a heart of a patient is provided. A cardiac access channel is established through an apical wall of the heart to provide direct access through the apical wall to the left ventricle. A vascular access channel is established through the skin to a peripheral blood vessel. A first end of an elongate member is advanced from the outside of the apical wall through the cardiac access channel and into the left ventricle. A second end disposed opposite the first end remains outside the patient. The elongate member is drawn into and through the vascular access channel to externalize the first end of the elongate member while leaving the second end outside the apical wall of the heart.

15 Claims, 19 Drawing Sheets

(52) U.S. Cl.
CPC .. *A61F 2/2427* (2013.01); *A61B 2017/00243* (2013.01); *A61B 2017/00247* (2013.01); *A61B 2017/00623* (2013.01); *A61B 2017/00632* (2013.01); *A61B 2017/3425* (2013.01)

(58) Field of Classification Search
CPC ........... A61B 2017/00252; A61B 2017/00256; A61B 2017/00623; A61B 2017/00646; A61B 2017/0065; A61B 2017/00654; A61B 2017/00659; A61B 2017/00663; A61B 2017/00668; A61F 2/2427
See application file for complete search history.

(56) References Cited

U.S. PATENT DOCUMENTS

| | | |
|---|---|---|
| 6,117,144 A | 9/2000 | Nobles et al. |
| 6,117,145 A | 9/2000 | Wood et al. |
| 6,136,010 A | 10/2000 | Modesitt et al. |
| 6,165,183 A | 12/2000 | Kuehn et al. |
| 6,197,043 B1 | 3/2001 | Davidson |
| 6,206,893 B1 | 3/2001 | Klein et al. |
| 6,269,819 B1 | 8/2001 | Oz et al. |
| 6,287,321 B1 | 9/2001 | Jang |
| 6,312,446 B1 | 11/2001 | Huebsch et al. |
| 6,312,447 B1 | 11/2001 | Grimes |
| 6,325,067 B1 | 12/2001 | Sterman et al. |
| 6,328,757 B1 | 12/2001 | Matheny |
| 6,461,366 B1 | 10/2002 | Seguin |
| 6,575,971 B2 | 6/2003 | Hauck et al. |
| 6,629,534 B1 | 10/2003 | St. Goar et al. |
| 6,635,068 B1 | 10/2003 | Dubrul et al. |
| 6,752,813 B2 | 6/2004 | Goldfarb et al. |
| 6,770,083 B2 | 8/2004 | Seguin |
| 6,926,715 B1 | 8/2005 | Hauck et al. |
| 6,932,792 B1 | 8/2005 | St. Goar et al. |
| 6,945,978 B1 | 9/2005 | Hyde |
| 7,048,754 B2 | 5/2006 | Martin et al. |
| 7,226,467 B2 | 6/2007 | Lucatero et al. |
| 7,563,267 B2 | 7/2009 | Goldfarb et al. |
| 7,569,062 B1 | 8/2009 | Kuehn et al. |
| 7,604,646 B2 | 10/2009 | Goldfarb et al. |
| 7,632,308 B2 | 12/2009 | Loulmet |
| 7,635,329 B2 | 12/2009 | Goldfarb et al. |
| 7,666,204 B2 | 2/2010 | Thornton et al. |
| 7,704,269 B2 | 4/2010 | St. Goar et al. |
| 7,736,388 B2 | 6/2010 | Goldfarb et al. |
| 7,811,296 B2 | 10/2010 | Goldfarb et al. |
| 7,828,819 B2 | 11/2010 | Webler et al. |
| 7,854,762 B2 | 12/2010 | Speziali et al. |
| 7,938,827 B2 | 5/2011 | Hauck et al. |
| 7,981,123 B2 | 7/2011 | Seguin |
| 8,123,703 B2 | 2/2012 | Martin et al. |
| 8,172,856 B2 | 5/2012 | Eigler et al. |
| 8,216,256 B2 | 7/2012 | Raschdorf, Jr. et al. |
| 8,216,302 B2 | 7/2012 | Wilson et al. |
| 8,303,608 B2 | 11/2012 | Goldfarb et al. |
| 8,323,334 B2 | 12/2012 | Deem et al. |
| 8,409,219 B2 | 4/2013 | Kelley et al. |
| 8,409,273 B2 | 4/2013 | Thornton et al. |
| 8,545,551 B2 | 10/2013 | Loulmet |
| 8,568,472 B2 | 10/2013 | Marchand et al. |
| 8,992,605 B2 | 3/2015 | Zakai et al. |
| 9,023,099 B2 | 5/2015 | Duffy et al. |
| 9,060,858 B2 | 6/2015 | Thornton et al. |
| 9,474,605 B2 | 10/2016 | Rowe et al. |
| 9,498,330 B2 | 11/2016 | Solem |
| 9,763,658 B2 | 9/2017 | Eigler et al. |
| 10,080,657 B2 | 9/2018 | Siegel |
| 10,105,221 B2 | 10/2018 | Siegel |
| 2001/0005787 A1 | 6/2001 | Oz et al. |
| 2002/0013571 A1 | 1/2002 | Goldfarb et al. |
| 2003/0120340 A1 | 6/2003 | Liska et al. |
| 2004/0044350 A1 | 3/2004 | Martin et al. |
| 2004/0260322 A1 | 12/2004 | Rudko et al. |
| 2005/0033446 A1 | 2/2005 | Deem et al. |
| 2005/0107871 A1 | 5/2005 | Realyvasquez et al. |
| 2005/0143811 A1 | 6/2005 | Realyvasquez |
| 2005/0222489 A1 | 10/2005 | Rahdert et al. |
| 2006/0020275 A1 | 1/2006 | Goldfarb et al. |
| 2006/0074484 A1* | 4/2006 | Huber .............. A61B 17/22004 623/2.11 |
| 2006/0229708 A1 | 10/2006 | Powell et al. |
| 2006/0293739 A1 | 12/2006 | Vijay |
| 2007/0032850 A1 | 2/2007 | Ruiz et al. |
| 2007/0038293 A1 | 2/2007 | St. Goar et al. |
| 2007/0055303 A1 | 3/2007 | Vidlund et al. |
| 2007/0270943 A1 | 11/2007 | Solem et al. |
| 2009/0048668 A1 | 2/2009 | Wilson et al. |
| 2009/0062836 A1* | 3/2009 | Kurrus ............. A61B 17/00491 606/195 |
| 2009/0076600 A1 | 3/2009 | Quinn |
| 2009/0177266 A1 | 7/2009 | Powell et al. |
| 2010/0022823 A1 | 1/2010 | Goldfarb et al. |
| 2010/0217283 A1 | 8/2010 | St. Goar et al. |
| 2010/0298929 A1 | 11/2010 | Thornton et al. |
| 2011/0029071 A1 | 2/2011 | Zlotnick et al. |
| 2011/0066233 A1 | 3/2011 | Thornton et al. |
| 2011/0106245 A1 | 5/2011 | Miller et al. |
| 2011/0218620 A1 | 9/2011 | Meiri et al. |
| 2011/0224655 A1 | 9/2011 | Asirvatham et al. |
| 2011/0264208 A1 | 10/2011 | Duffy et al. |
| 2011/0313437 A1 | 12/2011 | Yeh |
| 2011/0319989 A1 | 12/2011 | Lane et al. |
| 2012/0010700 A1 | 1/2012 | Spenser |
| 2012/0065464 A1 | 3/2012 | Ellis et al. |
| 2012/0078360 A1 | 3/2012 | Rafiee |
| 2012/0095547 A1 | 4/2012 | Chuter |
| 2012/0116418 A1 | 5/2012 | Belson et al. |
| 2012/0191181 A1 | 7/2012 | Kassab et al. |
| 2012/0245678 A1 | 9/2012 | Solem |
| 2012/0310331 A1 | 12/2012 | Eigler et al. |
| 2012/0310334 A1 | 12/2012 | Dolan |
| 2013/0018414 A1 | 1/2013 | Widimski et al. |
| 2013/0030522 A1 | 1/2013 | Rowe et al. |
| 2013/0197559 A1* | 8/2013 | Hariton .............. A61B 17/3415 606/185 |
| 2013/0226288 A1* | 8/2013 | Goldwasser ....... A61B 17/0057 623/2.1 |
| 2013/0253547 A1 | 9/2013 | Goldfarb et al. |
| 2013/0261739 A1* | 10/2013 | Kuehn ................. A61F 2/2412 623/2.11 |
| 2014/0039607 A1 | 2/2014 | Kovach |
| 2014/0058502 A1 | 2/2014 | Marchand et al. |
| 2014/0236198 A1 | 8/2014 | Goldfarb et al. |
| 2015/0038988 A1 | 2/2015 | Tegels et al. |
| 2015/0134057 A1 | 5/2015 | Rourke et al. |
| 2015/0173765 A1 | 6/2015 | Miller et al. |
| 2016/0000562 A1 | 1/2016 | Siegel |
| 2016/0008129 A1 | 1/2016 | Siegel |
| 2016/0324635 A1* | 11/2016 | Vidlund ................ A61F 2/2418 |
| 2017/0143478 A1 | 5/2017 | Schwartz et al. |
| 2017/0174979 A1 | 6/2017 | Sanders |
| 2017/0245988 A1 | 8/2017 | Siegel et al. |
| 2018/0193016 A1 | 7/2018 | Eigler et al. |
| 2019/0008638 A1 | 1/2019 | Siegel et al. |
| 2019/0076246 A1 | 3/2019 | Siegel |
| 2019/0298516 A1 | 10/2019 | Siegel et al. |

FOREIGN PATENT DOCUMENTS

| | | |
|---|---|---|
| EP | 3 269 330 | 1/2018 |
| WO | WO 00/60995 | 10/2000 |
| WO | WO 01/26557 | 4/2001 |
| WO | WO 01/070116 | 9/2001 |
| WO | WO 02/034167 | 5/2002 |
| WO | WO 03/049619 | 6/2003 |
| WO | WO 2004/012583 | 2/2004 |
| WO | WO 2005/058239 | 6/2005 |
| WO | WO 2007/011994 | 1/2007 |
| WO | WO 2011/116379 | 9/2011 |
| WO | WO 2014/138284 | 9/2014 |
| WO | WO 2014/138482 | 9/2014 |

(56) References Cited

FOREIGN PATENT DOCUMENTS

| WO | WO 2016/040526 | 3/2016 |
|----|----------------|--------|
| WO | WO 2016/077783 | 5/2016 |
| WO | WO 2017/015632 | 1/2017 |
| WO | WO 2018/140535 | 8/2018 |
| WO | WO 2019/152598 | 8/2019 |

OTHER PUBLICATIONS

Black MD, M., Division of Pediatric Cardiac Surgery, Standford University School of Medicine, California, USA, Minimally Invasive Pediatric Cardiac Surgery, Online Article in 4 pages.

Ethicon Wound Closure Manual—Chapter 6, Research and Development at Ethicon, Inc.—An Ongoing Process of Change and Improvement, Online at www.ethiconinc.com in 4 pages.

Gersak MD, Ph.D., B., "Mitral Valve Repair or Replacement on the Beating Heart", The Heart Surgery Forum #2000-1989, Jun. 8, 2000, pp. 232-237, 2000 Forum Multimedia Publishing, LLC.

Perclose A-T, 6F Suture-Mediated Closure (SMC) System, Instructions for Use disctributed in the U.S. by Abbott laboratories, Inc. 2002, 2006 Abbott Laboratories in 11 pages.

Quealy et al., "Use of Combined Intravascular Ultrasound and PTCA Catheter: Clinical Utility", Chapter 12, pp. 245-250.

International Search Report and Written Opinion issued in PCT Application No. PCT/US2015/060726, dated Mar. 4, 2016, in 16 pages.

International Preliminary Report on Patentability issued in PCT Application No. PCT/US2015/060726, dated May 16, 2017, in 10 pages.

* cited by examiner

CARDIOVASCULAR ACCESS AND DEVICE DELIVERY SYSTEM

CROSS-REFERENCE TO RELATED APPLICATIONS

This application is a national stage application under 35 U.S.C. § 371 of International Application No. PCT/US2015/060726, filed on Nov. 13, 2015, which published in English as WO 2016/077783 A1 on May 19, 2016, and which claims priority benefit of U.S. Patent Application No. 62/079,811, filed on Nov. 14, 2014.

BACKGROUND OF THE INVENTION

Field of the Invention

This application is directed to systems and methods for accessing heart chambers or major blood vessels to facilitate delivering and implanting devices or performing therapies therein.

Description of the Related Art

Catheters are in widespread use for a wide number of procedures. In recent years, complex devices such as aortic valves have been delivered using catheters. These catheter based procedures provide benefits for patients, including reduced trauma compared to surgical techniques for accomplishing similar outcomes, e.g., aortic valve replacement.

Limitations of catheter based techniques have spurred efforts to develop a less invasive surgical technique that can be performed through cannulae inserted into the heart through the chest wall and through an apical puncture in the heart. These procedures have advantages, such as moving the proximal end of the tools used to perform the procedure closer to the surgical site.

These surgical approaches provide various disadvantages, however. For one, access to the heart through the chest wall is more complex than access to a superficial peripheral vessel, such as a femoral artery. For example, a surgical window must still be opened to advance the surgical cannulae through the skin and intervening tissue to the heart. To the extent large devices are delivered through this enlarged surgical window, trauma to the patient is increased and closure of the heart puncture is challenging.

SUMMARY OF THE INVENTION

The methods and systems herein provide low-profile access for creating a trans-cardiac rail with two externalized ends.

In one embodiment, a method of accessing a heart of a patient is provided. The method can be used to provide a treatment, which may involve implanting a prosthesis or other implant. A cardiac access channel is established through an apical wall of the heart to provide direct access through the apical wall to the left ventricle. A vascular access channel is established through the skin to a peripheral blood vessel. A first end of an elongate member is advanced from the outside of the apical wall through the cardiac access channel and into the left ventricle. A second end disposed opposite the first end remains outside the patient. The elongate member is drawn into and through the vascular access channel to externalize the first end of the elongate member while leaving the second end outside the apical wall of the heart.

In another embodiment, a method of accessing a heart is provided. Vascular access is provided at a peripheral vein. An access catheter is advanced through the peripheral vein, through the vena cava, and into the heart. A distal portion of the access catheter is advanced across the intra-atrial septum into the left atrium. A channel is established through a wall of the heart to provide direct access through the wall to the left ventricle. An elongate member is advanced through the channel into the left ventricle. The elongate member is drawn into the access catheter. The elongate member is tensioned between the distal portion of the access catheter and the channel.

In another embodiment, a method of accessing a heart is provided. Vascular access is provided at a peripheral artery. An access catheter is advanced into the aorta through the peripheral artery. In some embodiments, the access catheter passes through the brachial artery and the left subclavian artery. In some embodiments, the access catheter passes through a femoral artery and an iliac artery. In some embodiments, the elongate member advances antegrade from the ventricle into the aorta. In some embodiments, the elongate member advances into the subclavian artery or iliac artery. In at least one embodiment, the elongate member includes an atraumatic tip such as a floppy tip, a "J" tip, or a balloon tip.

In another embodiment, a method of placing a cardiovascular prosthesis is provided. A delivery system is advanced percutaneously from a peripheral blood vessel access site into the left atrium of a heart. The left ventricle is accessed from outside the heart through the wall of the heat at or adjacent to the apex of the heart by placing a sheath therethrough. An elongate member is advanced through the sheath across the aortic valve. The delivery system is linked with the elongate member to provide a venous-arterial rail for delivery of a prosthesis into the heart and/or the aorta. A condition in the heart and/or arterial vasculature is treated over the venous-arterial rail.

In another embodiment, a device for closing a cardiac access channel is provided. The device comprises an elongate body having a proximal end and a distal end. The proximal end has a first opening for delivering a closure medium and a second opening for delivering a pressurizing medium. The distal end has a first fillable member that comprises a distal face, an enclosure disposed at the distal face and extending proximally therefrom, and one or more pores disposed through the enclosure at the distal face thereof. The first fillable member is in fluid communication with the first opening such that the closure medium can be delivered to the first fillable member. The distal end has a second fillable member in fluid communication with the second opening such that the pressuring medium can be delivered to the second fillable member. The first and second fillable members are arranged such that when the first fillable member contains the closure medium and the second fillable member contains the pressurizing medium, the closure medium is disposed through the pore(s).

BRIEF DESCRIPTION OF THE DRAWINGS

A more complete appreciation of the subject matter of this application and the various advantages thereof can be realized by reference to the following detailed description, in which reference is made to the accompanying drawings in which.

More detailed descriptions of various embodiments of catheter based and transapical delivery systems, components and methods useful to treat patients are set forth below.

DETAILED DESCRIPTION OF THE PREFERRED EMBODIMENT

This application discloses various system and methods for providing a rail structure for guiding the advancement and deployment of cardiac prostheses or therapy devices. The rail structure preferably has two or more ends that are externalized. Externalized ends may include portions that are disposed outside the body, such as through percutaneous vascular access device or through direct cardiac access device. Intracorporeal lengths of the rail may be disposed between the externalized ends. FIGS. 1-5 illustrate systems and methods that provide a rail structure between a direct heart access and a peripheral blood vessel access site. FIG. 6 shows a variation where a rail structure is disposed between a direct heart access and a peripheral arterial access. FIGS. 7-14 illustrate systems and methods for closing a heart wall puncture. FIGS. 15-19 illustrate systems and methods that can be used to provide a rail between an externalized end at a peripheral venous site and an externalized end at a peripheral arterial site. The methods and systems of FIGS. 15-19 exploit the use of direct heart access to facilitate various techniques.

Figure 1:
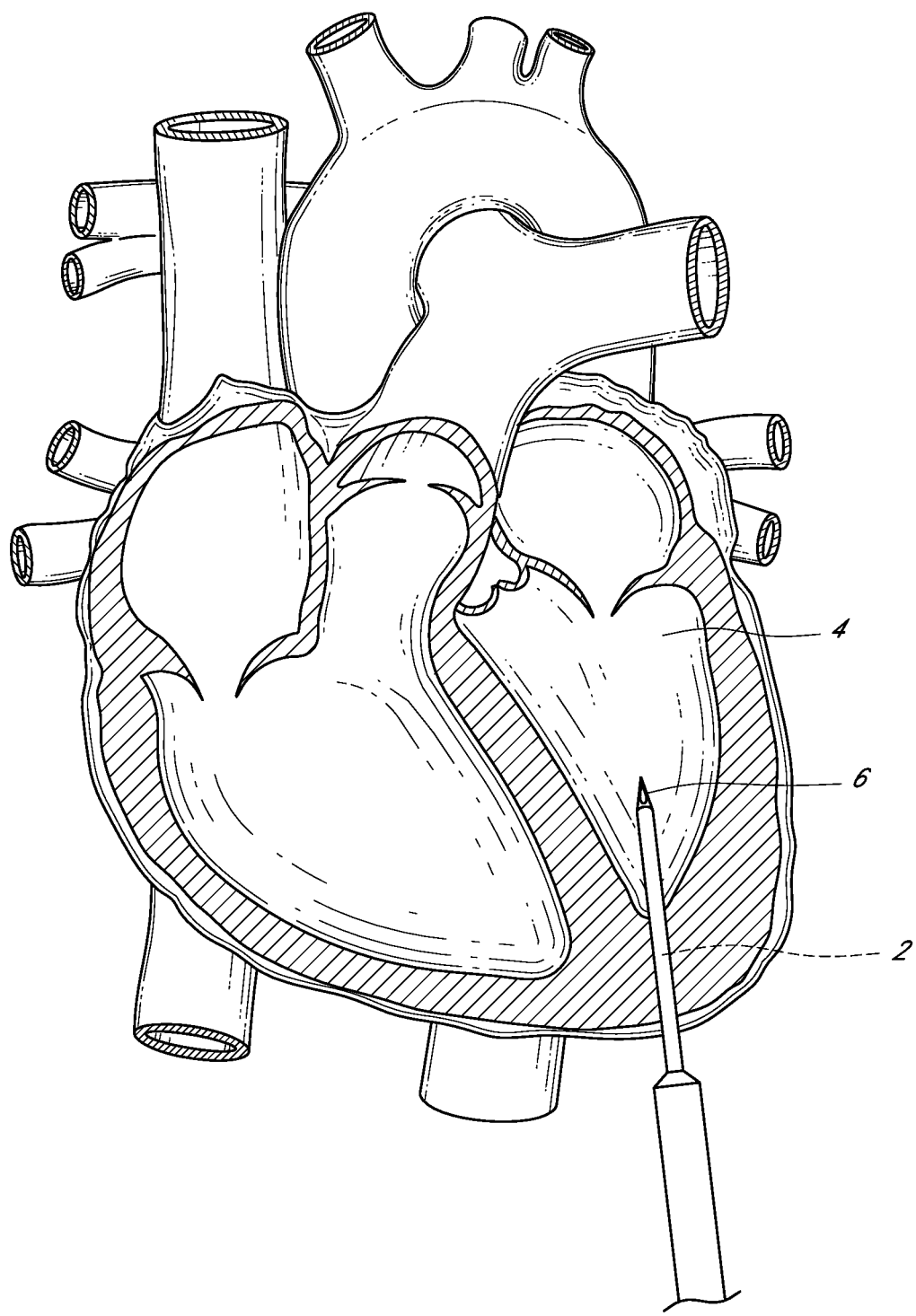
FIG. 1 is a cross-sectional view of a heart showing a needle placed through the apex of the heart into the left ventricle to provide access to the ventricle.

I. Direct Heart Access to Facilitate a Venous-to-Apex or Arterial-to-Apex Rail FIGS. 1-6 illustrate a method of accessing a heart. FIG. 1 illustrates a channel 2 established through a wall of the heart to provide direct access through the wall to the left ventricle 4. Prior to establishing the channel 2 through the heart, surgical access is provided to the outside of the heart. For example, a minimally invasive technique can be provided to expose the apex of the heart. The minimally invasive technique may involve spreading two or more ribs to provide for direct visualization of the heart. In some embodiments, the channel 2 is established with a small-profile needle 6. That is, the needle 6 may be inserted from the outside of the heart through the myocardium and into the left ventricle as shown. In at least one embodiment, the channel 2 is established using an 18-gauge, beveled needle. In some embodiments, the needle 6 includes a collapsible sheath to establish the channel 2 through the heart wall.

Figure 2:
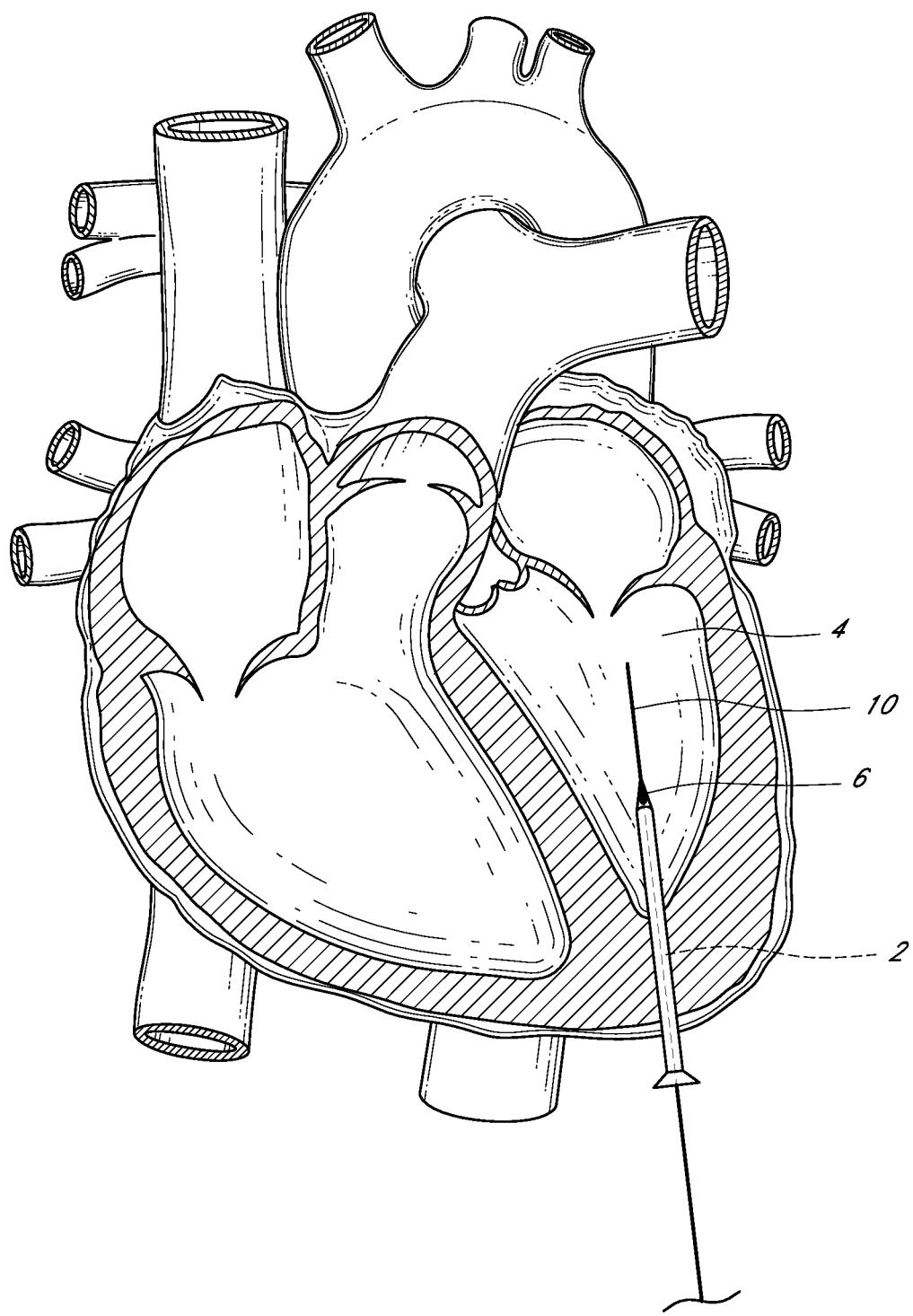
FIG. 2 shows an elongate member disposed through the needle and into the left ventricle.

FIG. 2 shows an elongate member 10 advanced through the channel 2 into the left ventricle 4. For example, the elongate member 10 can be inserted such that a distal end thereof is advanced through the needle 6 into the ventricle as shown. The proximal end can remain outside the patient at this stage. The elongate member 10 can be similar to a stiff guidewire. In some embodiments, the elongate member 10 has a flow directed device such as a small balloon disposed at the distal end thereof.

Figure 3:
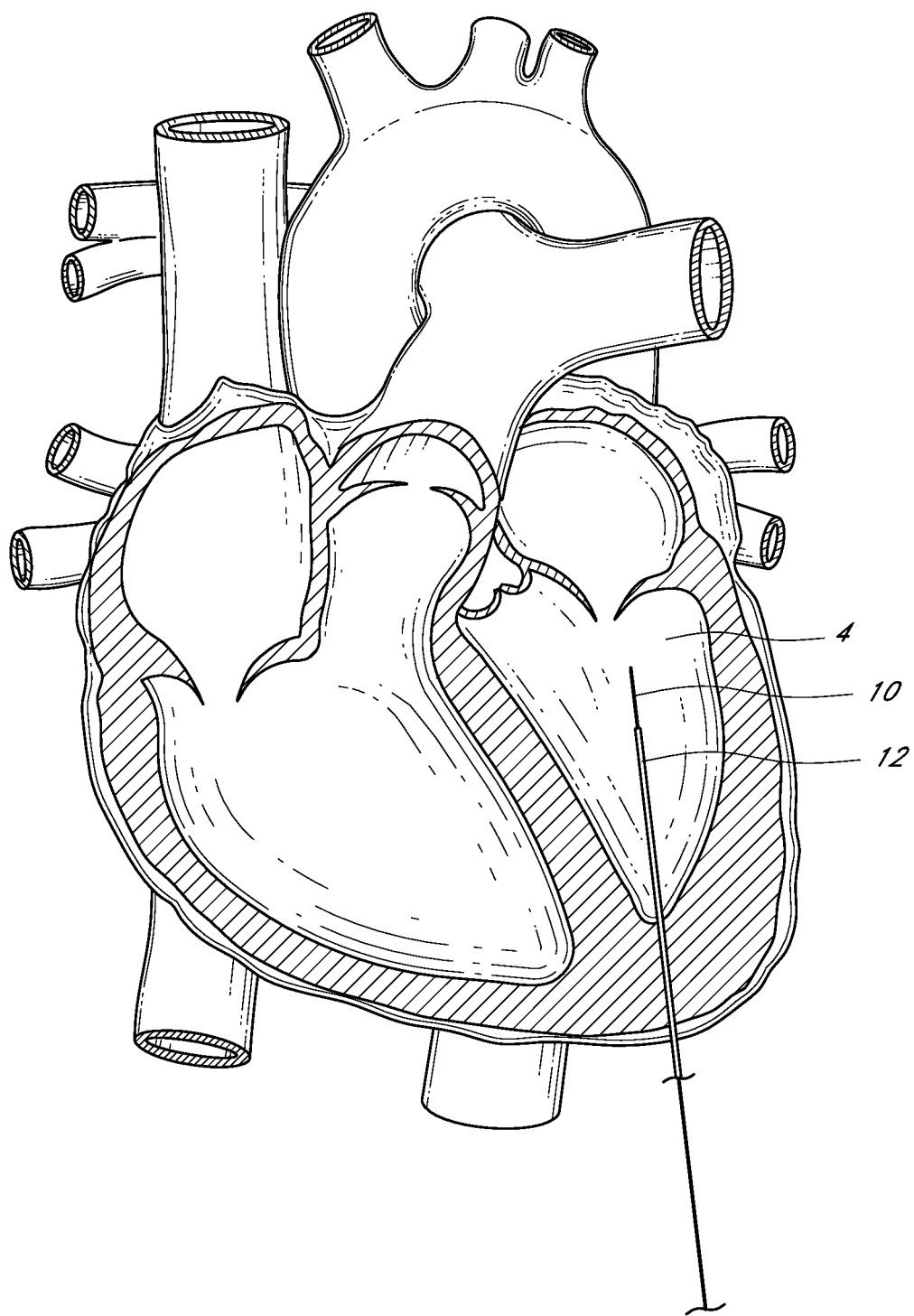
FIG. 3 illustrates an introducer sheath disposed transapically over the elongate member into the ventricle.

FIG. 3 shows the needle 6 can be removed after the elongate member 10 is advanced into the left ventricle 4. In some embodiments, an introducer sheath or other spanning sheath 12 is fitted over the elongate member 10 and advanced over the elongate member 10 until the spanning sheath 12 spans across the heart wall. In some embodiments, the spanning sheath 12 is a low-profile sheath. In some embodiments, the spanning sheath is a 4 or a 5 French sheath. In some embodiments, the spanning sheath is 16-gauge or 18-gauge. Preferably the spanning sheath 12 is configured to limit or prevent backflow of blood out of the ventricle which is a high pressure chamber.

Figure 4:
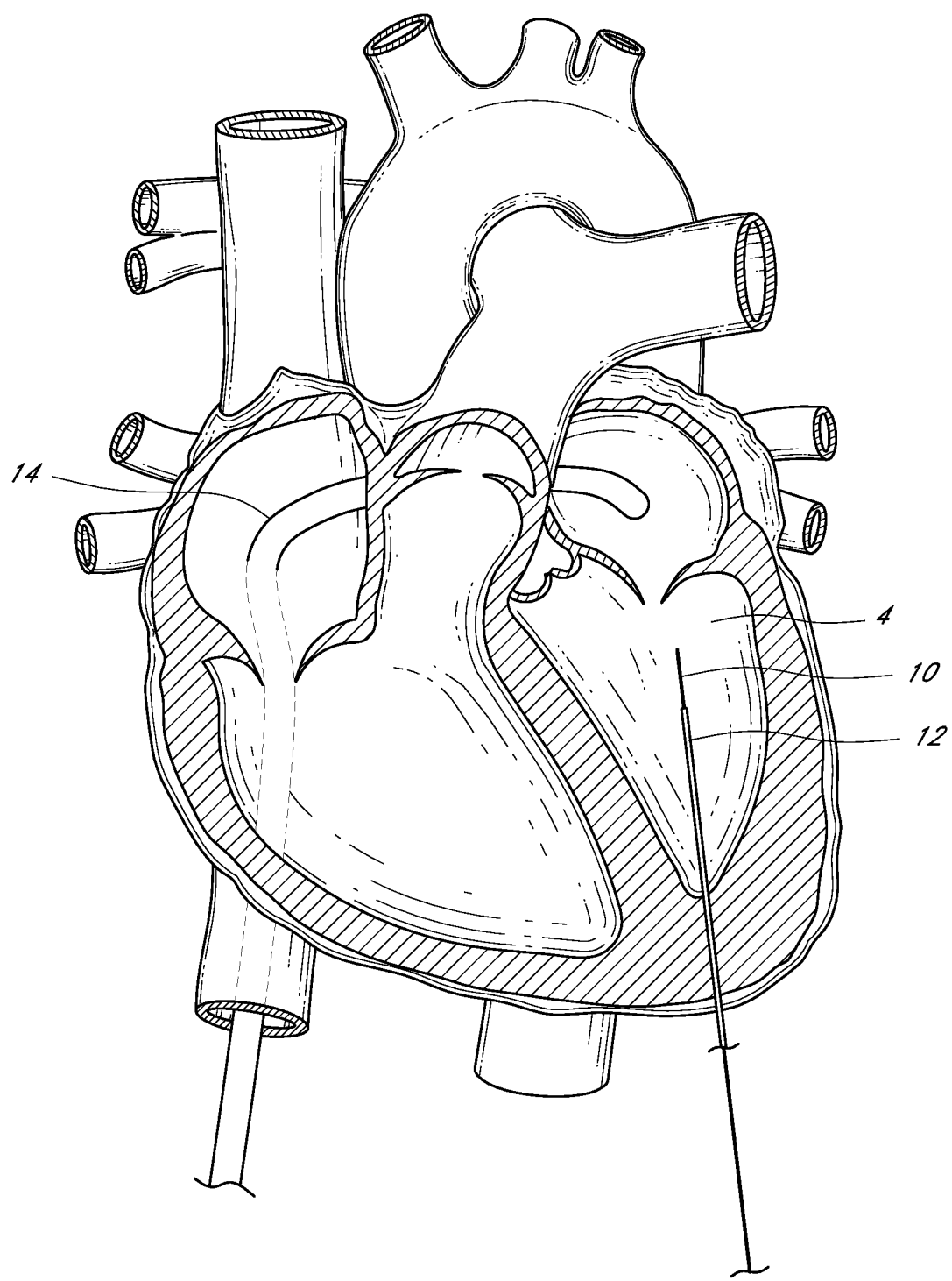
FIG. 4 illustrates an access catheter disposed from venous vasculature into the heart.
Figure 5:
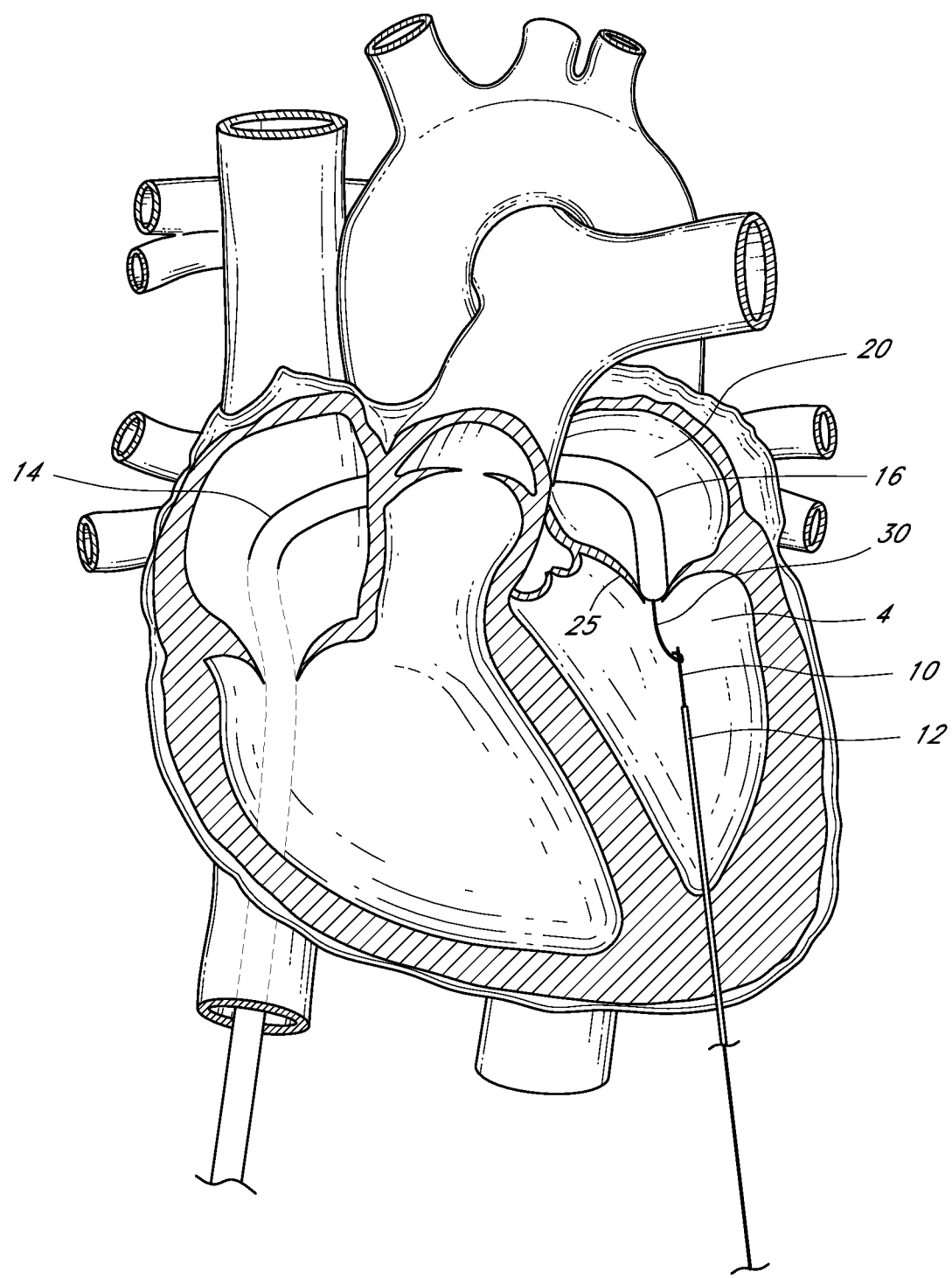
FIG. 5 illustrates the elongate member illustrated in FIG. 2 engaged by a snare and drawn toward or into the access catheter of FIG. 4 to provide a delivery platform through the mitral valve.
Figure 6:
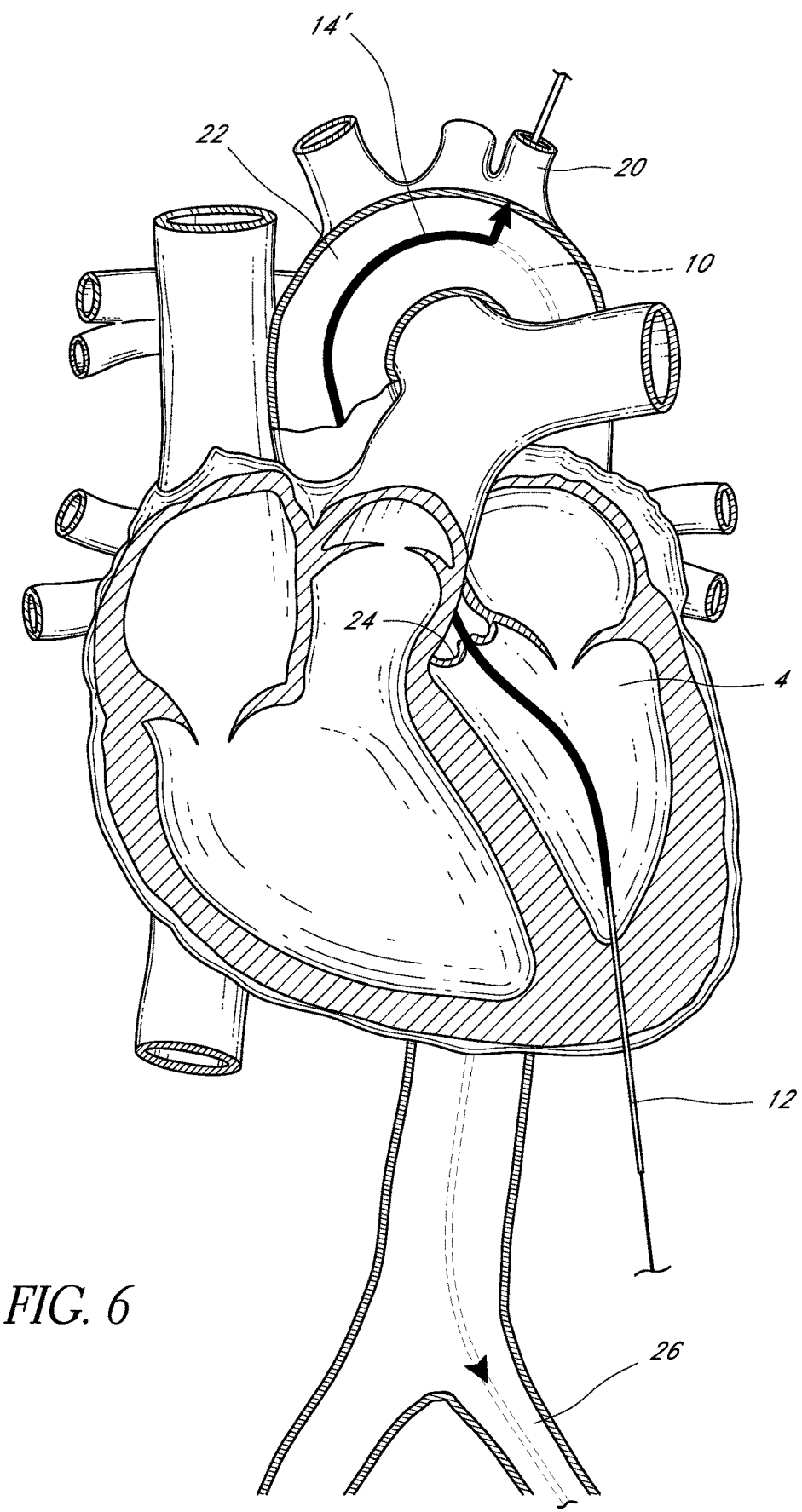
FIG. 6 illustrates providing a delivery platform between a direct heart access and one or more of a plurality of possible peripheral arterial sites.

FIGS. 4-6 illustrate methods of vascular access, whereby an access catheter can be advanced from a peripheral venous site to the heart. FIG. 4 illustrates an access catheter 14 advanced through venous vascular path, e.g., from a femoral or other peripheral vein, through the inferior or superior vena cava, and into the heart.

FIG. 5 shows a distal portion 16 of the access catheter 14 is advanced across the intra-atrial septum into the left atrium 20. In one method, the elongate member 10 is drawn into the access catheter 14. In some embodiments, the distal portion 16 of the access catheter 14 may include a means for capturing the elongate member 10. In at least one embodiment, a snare 30 extends from the distal portion 16 of the access catheter 14 and entraps or captures the elongate member 10. The elongate member 10 is then drawn into the access catheter 14. The elongate member 10 can be tensioned between the distal portion 16 of the access catheter 14 and the channel 2. Alternatively, the access catheter 14 may be modified such as by being shortened and/or equipped with appropriate valves to be introduced through the left atrial wall using access methods discussed in U.S. Patent Application Publication Number US 2013/0041395, which is incorporated herein by reference. Further details of performing procedures using a taught platform between the access catheter 14 as illustrated or modified and a ventricle wall (e.g., with a base or footing deployed adjacent to an inner surface of the ventricle wall, with tines at least partially embedded in the wall, or with a trans-apical channel) are discussed in International Publication Number WO 2014/138284, which is incorporated herein by reference.

In some embodiments, the venous-to-apex rail is used to deploy a prosthesis (not shown) to the mitral valve 25. A venous-to-apex rail is established as shown above in FIG. 5. Tension is applied through the elongate member 10 in the apical direction, e.g., by pulling on the proximal externalized end, to draw the prosthesis from the access catheter 14. In some embodiments, the prosthesis is delivered by a second catheter (not shown), which is threaded over the venous-to-apex rail. In at least one embodiment, the venous-to-apex rail passes through the lumen of the prosthesis and is used to assist in seating the prosthesis onto the mitral valve 25. In some embodiments, the prosthesis is deployed between the anterior and posterior mitral valve leaflets at the level of the mitral valve annulus. In at least one embodiment, the prosthesis is deployed by expanding a balloon within the lumen of the prosthesis to seat the prosthesis in the mitral valve annulus. In some embodiments, the prosthesis is deployed by retracting a sheath to expose the prosthesis and to permit the prosthesis to expand into secure engagement with the mitral valve annulus.

In some embodiments, the venous-to-apex rail is used to deploy an annuloplasty ring. Annuloplasty rings are discussed in U.S. Pat. No. 5,888,240, which is incorporated herein by reference. In some embodiments, an annuloplasty ring is deployed alternatively or in addition to seating a prosthesis onto the mitral valve 25.

FIG. 6 illustrates alternative embodiment, in which a rail with two externalized ends is provided between the apical access site discussed above and a peripheral artery. A path 14' is shown, through which the elongate member 10 can travel to establish a rail that can be externalized at a peripheral artery. An arterial access catheter disposed at a peripheral location is advanced through the skin disposed over a peripheral artery and into the peripheral artery. In some embodiments, the arterial access catheter is introduced at a brachial artery and can be passed through the left subclavian artery 20, as illustrated in FIG. 6 by the solid line that extends through the left subclavian artery 20. In at least one embodiment, the arterial access catheter can be introduced at a femoral artery, and passed through the iliac artery 26, as illustrated in FIG. 6 by the dashed line that extends through the iliac artery 26. In some embodiments, the elongate member 10 is advanced antegrade into the aorta and/or into more distal arteries, to be drawn into the arterial access catheter. In some embodiments, the elongate member 10 is advanced antegrade into the subclavian artery 20, where a snare disposed through the arterial access catheter couples with elongate member 10. In at least one embodiment, the elongate member 10 is advanced antegrade into the iliac artery 26, where a snare disposed through the arterial access catheter couples with elongate member 10. After the snare or other capturing device disposed through the access catheter couples with the elongate member 10, the distal end of the elongate member 10 is drawn out of (e.g., externalized at) the arterial access site.

Thus, the path 14' defines two example routes for an apex to arterial rail structure. The route to the subclavian artery 20 is advantageous in providing a straighter path and is more suitable for smaller and/or lower profile devices. The route to the iliac artery 26 is advantageous for larger and/or higher profile devices that, by virtue of the rail structure provided by the elongate member 10, can easily track the relatively more tortuous path to the heart. Other peripheral sites could be used to externalize the distal end of the elongate member 10.

II. Closure Systems and Methods for Small-Bore Apex Access

Figure 7:
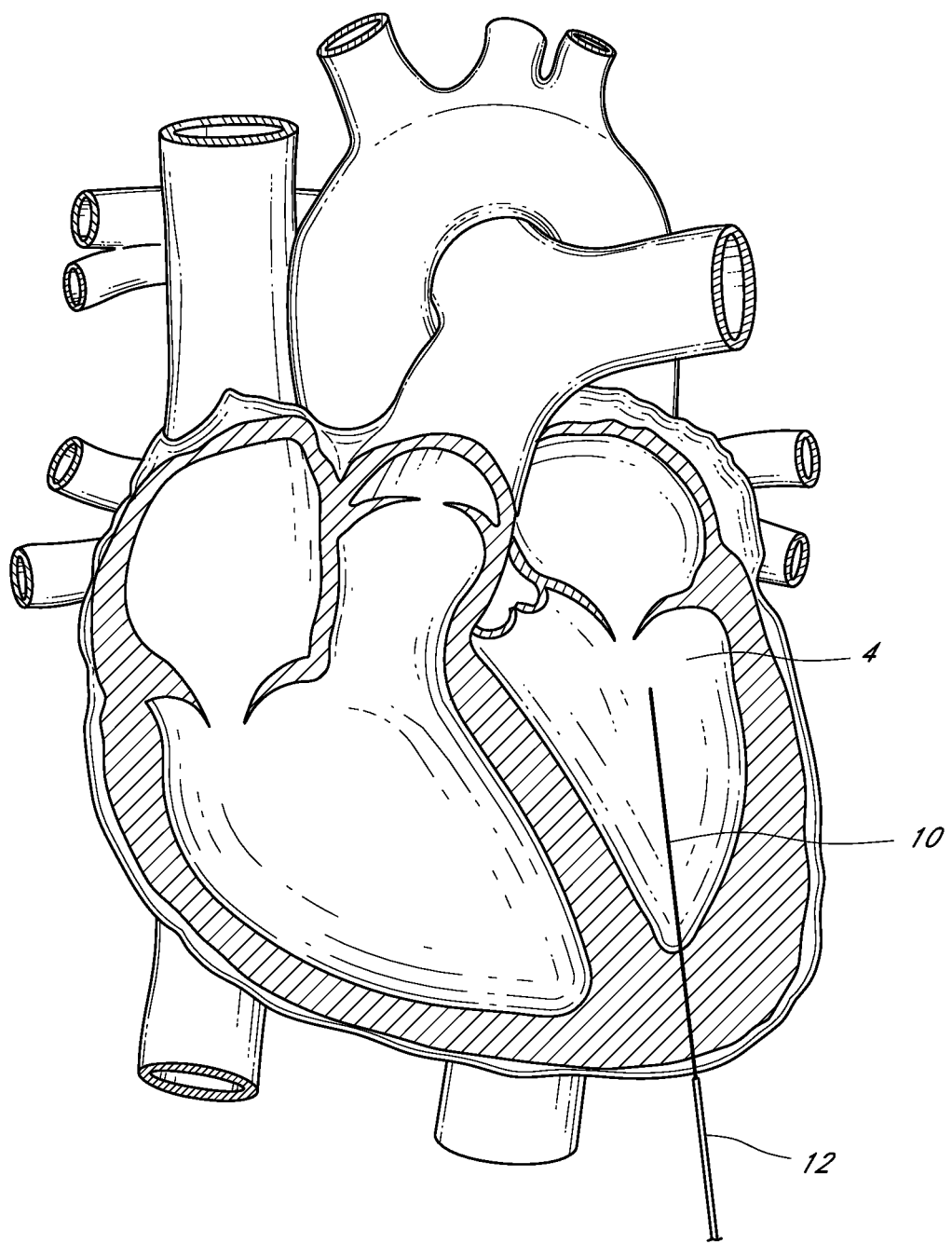
FIG. 7 illustrates removing the introducer sheath leaving the elongate member in place.

FIGS. 7-14 show methods for closing the apical site through which the elongate member 10 entered the left ventricle 4. FIG. 7 shows that in one method the spanning sheath 12 is first removed from the apex of the left ventricle 4. If no bleeding results after removal of the spanning sheath 12, the elongate member 10 is then removed from the heart. In some embodiments, the myocardium is sutured at the site of apical access to compress the tissue and close the site of apical access.

Figure 8:
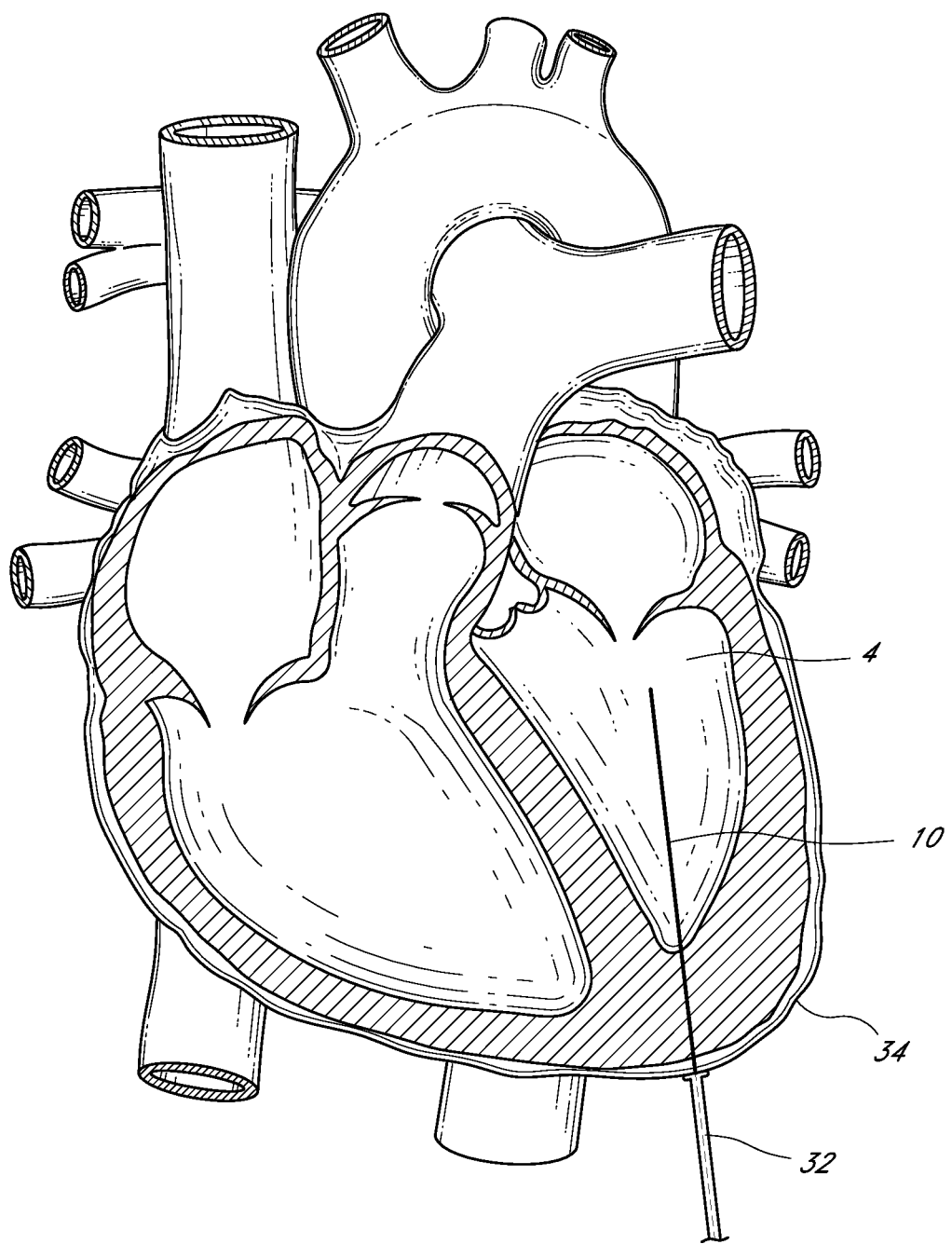
FIG. 8 illustrates placing a closure device over the elongate member to a position adjacent to the epicardium.

FIGS. 8-14 show methods for reducing bleeding that follows removal of the spanning sheath 12. FIG. 8 illustrates an embodiment where a compression member 32 is advanced over the proximal portion of the elongate member 10 until the compression member 32 contacts the heart. In some embodiments the compression member 32 includes means to introduce biological glue onto the epicardial surface 34 of the left ventricle 4. In some embodiments, the compression member 32 is held against the epicardial surface 34 for 30 seconds to 5 minutes to reduce bleeding. After bleeding has been reduced, the compression member 32 is withdrawn from epicardial surface 34 and the elongate member 10 is removed from the heart.

Figure 9:
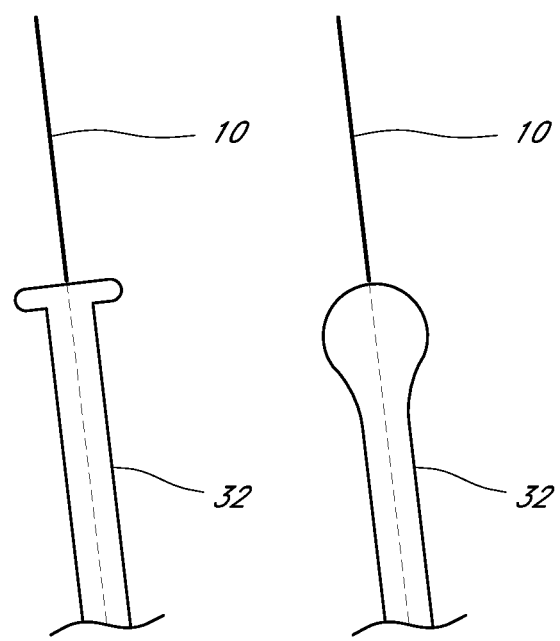
FIG. 9 illustrates one embodiment of a closure device configured to facilitate closure of a small puncture of the apex of the heart wall.
Figure 10:
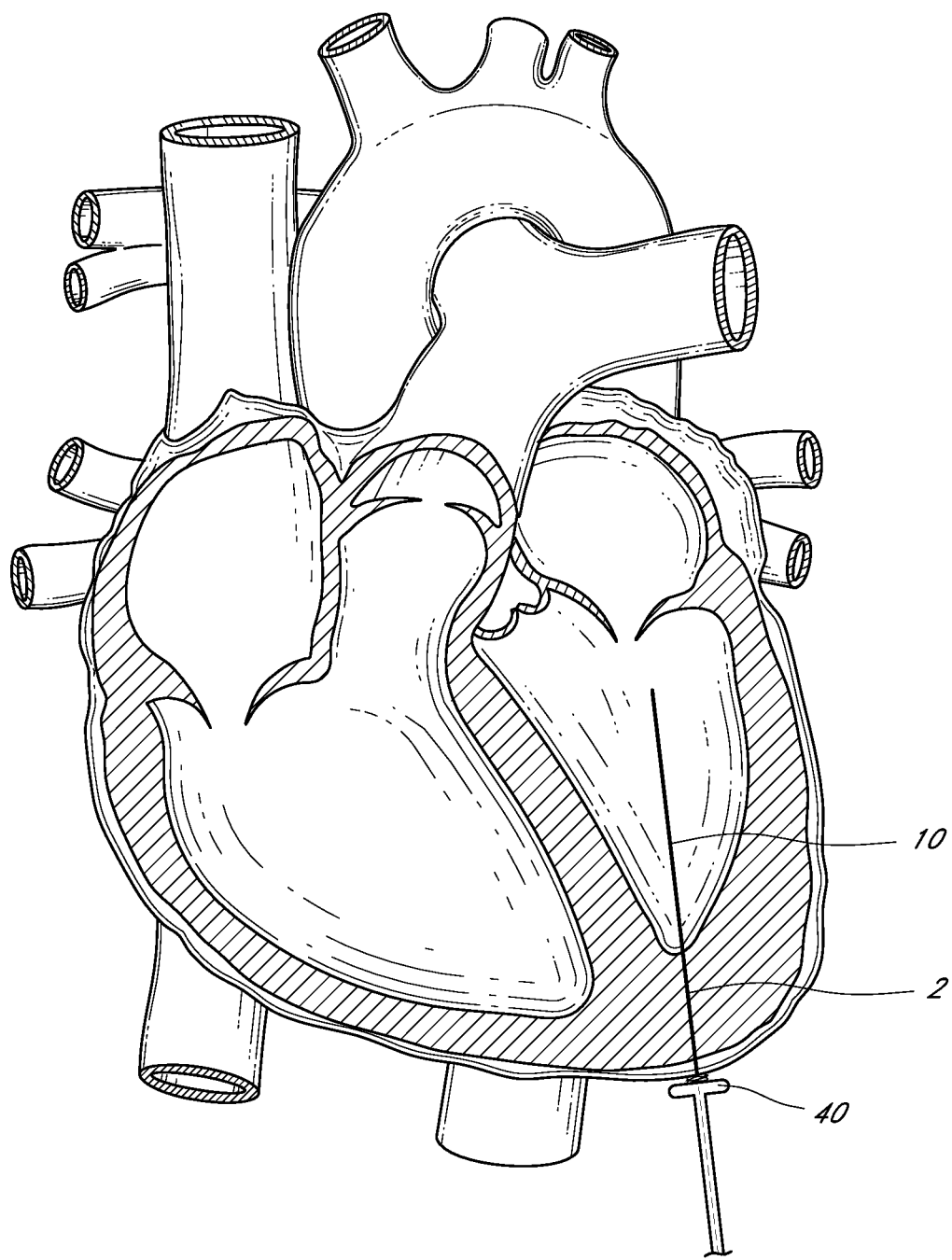
FIG. 10 illustrates another embodiment of a closure device that includes a disc shaped balloon to reduce or eliminate bleeding through the heart wall into the pericardium.

FIG. 9 illustrates various configurations of the compression member 32. In some embodiments, the compression member 32 is blunt-tipped. In some embodiments, the compression member 32 is disc-shaped.

Figure 11:
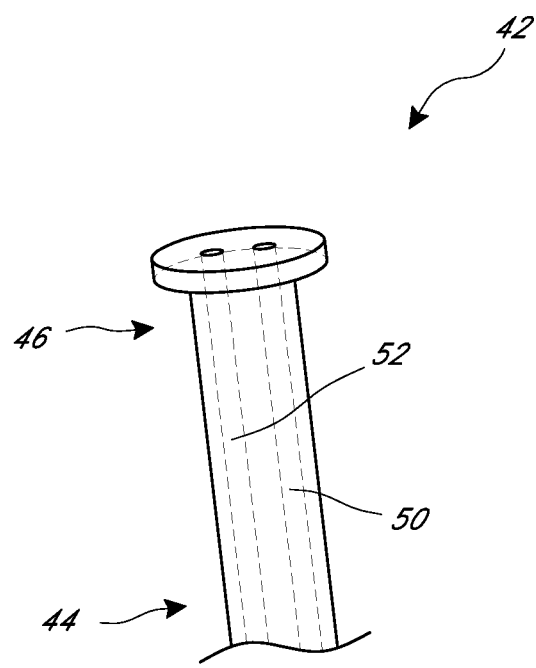
FIG. 11 illustrates another embodiment of a closure device, having a dual chamber configuration to dispense a closure medium.
Figure 12:
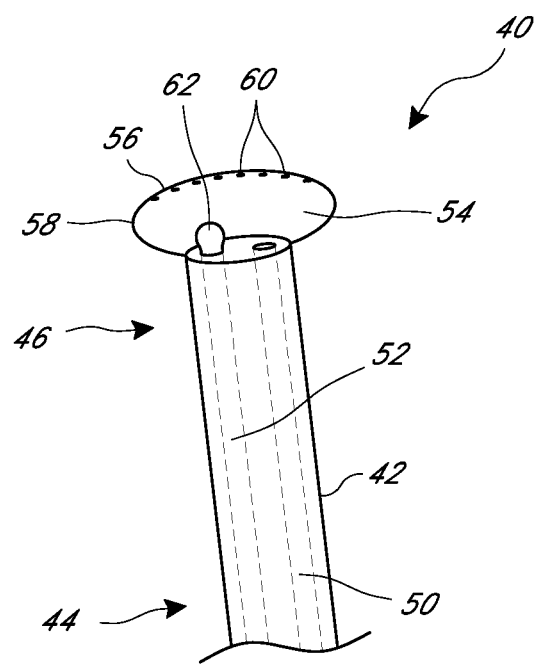
FIG. 12 illustrates a configuration of the closure device of FIG. 10 showing an outer chamber having a closure medium disposed therein and an inner chamber being in a low profile states.
Figure 13:
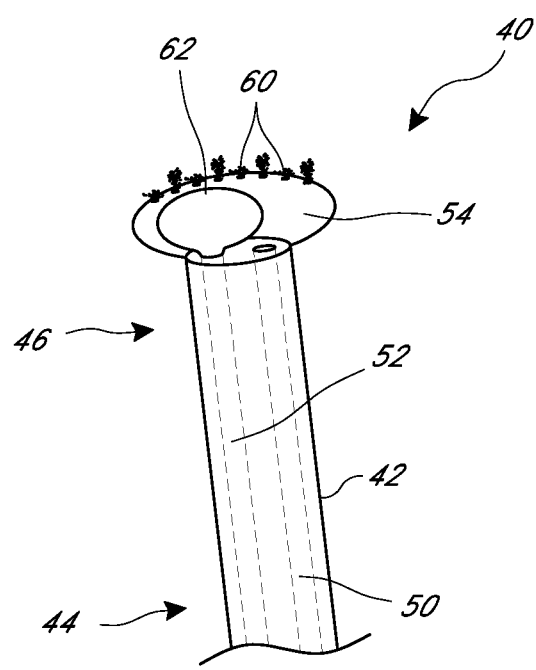
FIG. 13 illustrates the closure device of FIG. 10 with the inner chamber in a high profile state, e.g., inflated, to enhance the pressure in the outer chamber.
Figure 14:
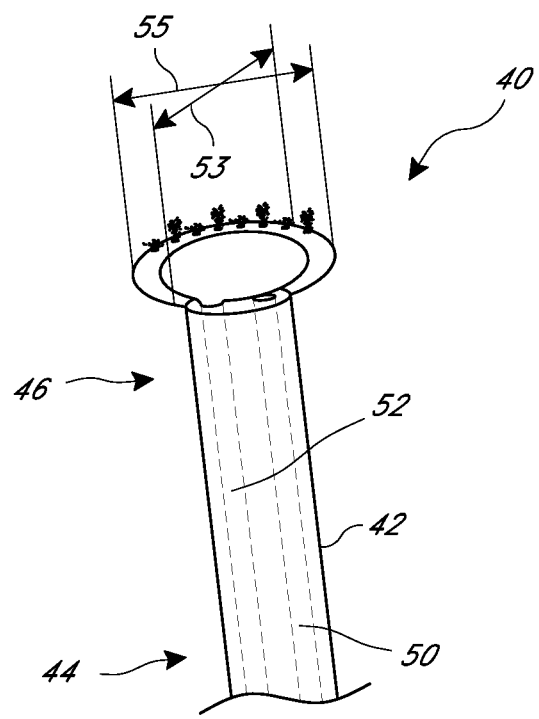
FIG. 14 illustrates the closure device of FIG. 10 with the inner chamber in a further high profile state, e.g., further inflated, to cause the closure medium to seep out of a distal face of the outer chamber.
Figure 15:
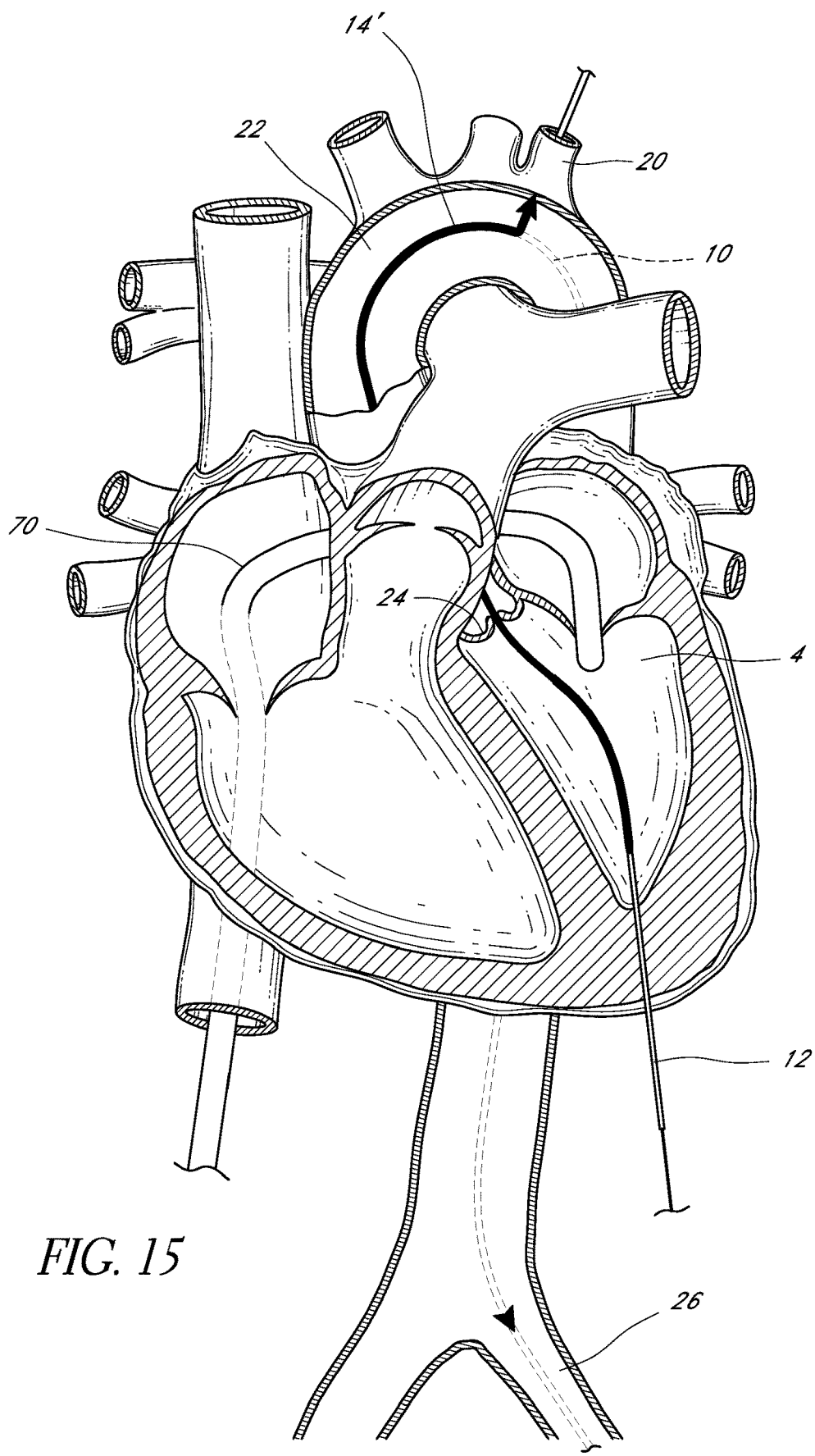
FIG. 15-17 illustrate providing a delivery platform between peripheral venous and peripheral arterial access sites, facilitated by direct heart access.

FIGS. 10-14 illustrate a device 40 for closing a cardiac access channel 2. The device 40 provides for controlled dispensing of a closure medium in the pericardium or onto the epicardium. Referring to FIGS. 11 and 12, the device 40 comprises an elongate body 42 having a proximal end 44 and a distal end 46. The proximal end 44 has a first opening 50 for delivering a closure medium and a second opening 52 for delivering a pressurizing medium. The distal end 46 has a first fillable member 54 that comprises a distal face 56, an enclosure 58 disposed at the distal face 56 and extending proximally therefrom, and one or more pores 60 disposed through the enclosure 58 at the distal face 56 thereof. In some embodiments, the distal face 56 has first and second traverse dimensions 53, 55 that are larger than cardiac access channel to be closed. In at least one embodiment, the first and second traverse dimensions 53, 55 are at least four times the size of the cardiac access channel to be closed. In at least one embodiment the first and second traverse dimensions 53, 55 are at least 12 mm.

The first fillable member 54 is in fluid communication with the first opening 50 such that the closure medium can be delivered to the first fillable member 54. The distal end 46 has a second fillable member 62 in fluid communication with the second opening 52 such that the pressuring medium can be delivered to the second fillable member 62. The first and second fillable members 54, 62 are arranged such that when the first fillable member 54 contains the closure medium and the second fillable member 62 contains the pressurizing medium, the closure medium is disposed through the pore(s) 60.

III. Direct Heart Access to Facilitate a Venous-Arterial Rail

Figure 16:
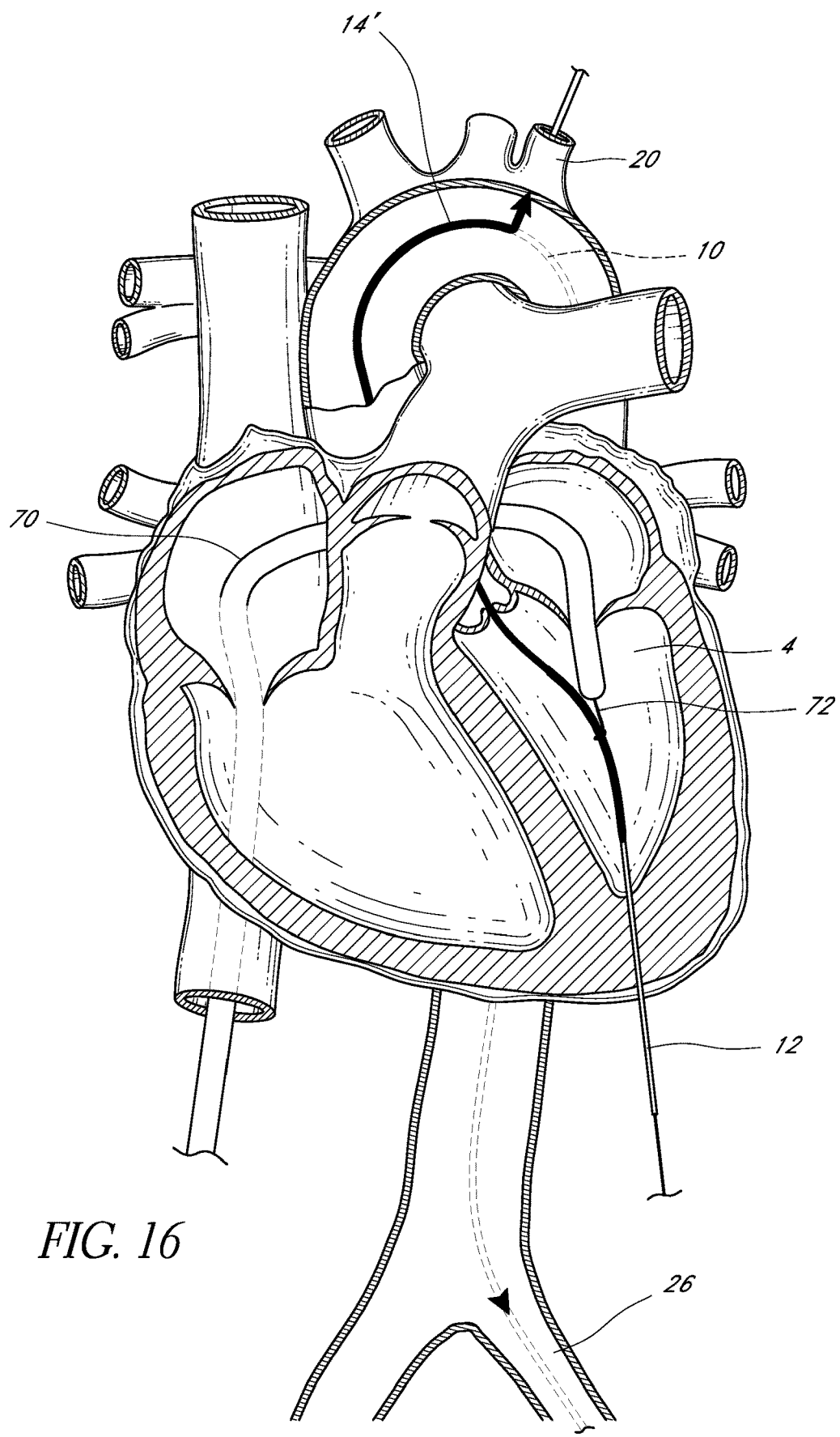

FIGS. 15-19 illustrate a method of placing a cardiovascular prosthesis that can be used for cardiac devices and also for deploying devices in the aorta and other large vessels close to the heart. A delivery system 70 is advanced percutaneously from a peripheral blood vessel access site into the left atrium of a heart. The left ventricle is accessed from outside the heart through the wall of the heart at or adjacent to the apex of the heart by placing a spanning sheath 12 therethrough. An elongate member 10 is advanced through the spanning sheath 12. An arterial access catheter is introduced into or through a peripheral artery. The elongate member 10 is advanced antegrade, and is captured by or through the access catheter, for example by a snare that couples with the elongate member 10, as described above. The elongate member 10 is drawn into the arterial access catheter after traversing one branch of the path 14' (e.g., into the subclavian or into the iliac). FIG. 16 shows that the elongate member 10 is also captured by a snare or loop 72 or similar structure that is extended from the distal portion 16 of the access catheter 14. FIG. 16 shows the delivery system 70 is linked with the elongate member 10 to provide a venous-arterial rail for delivery of a prosthesis into the heart and/or the aorta.

In some embodiments, the delivery system 70 accesses the left atrium through the left atrial wall using methods discussed in U.S. Patent Application Publication Number US 2013/0041395, which is incorporated herein by reference. In some embodiments, a delivery system 70 that accesses the left atrium through the left atrial wall is used to deploy a taught ventricular platform extending to a position adjacent an inner wall of the ventricle, extending to a position at least partially embedded in a wall about a ventricle, or extending completely through a ventricle wall as in a transapical channel as discussed in International Publication Number WO 2014/138284, which is incorporated herein by reference.

Figure 17:
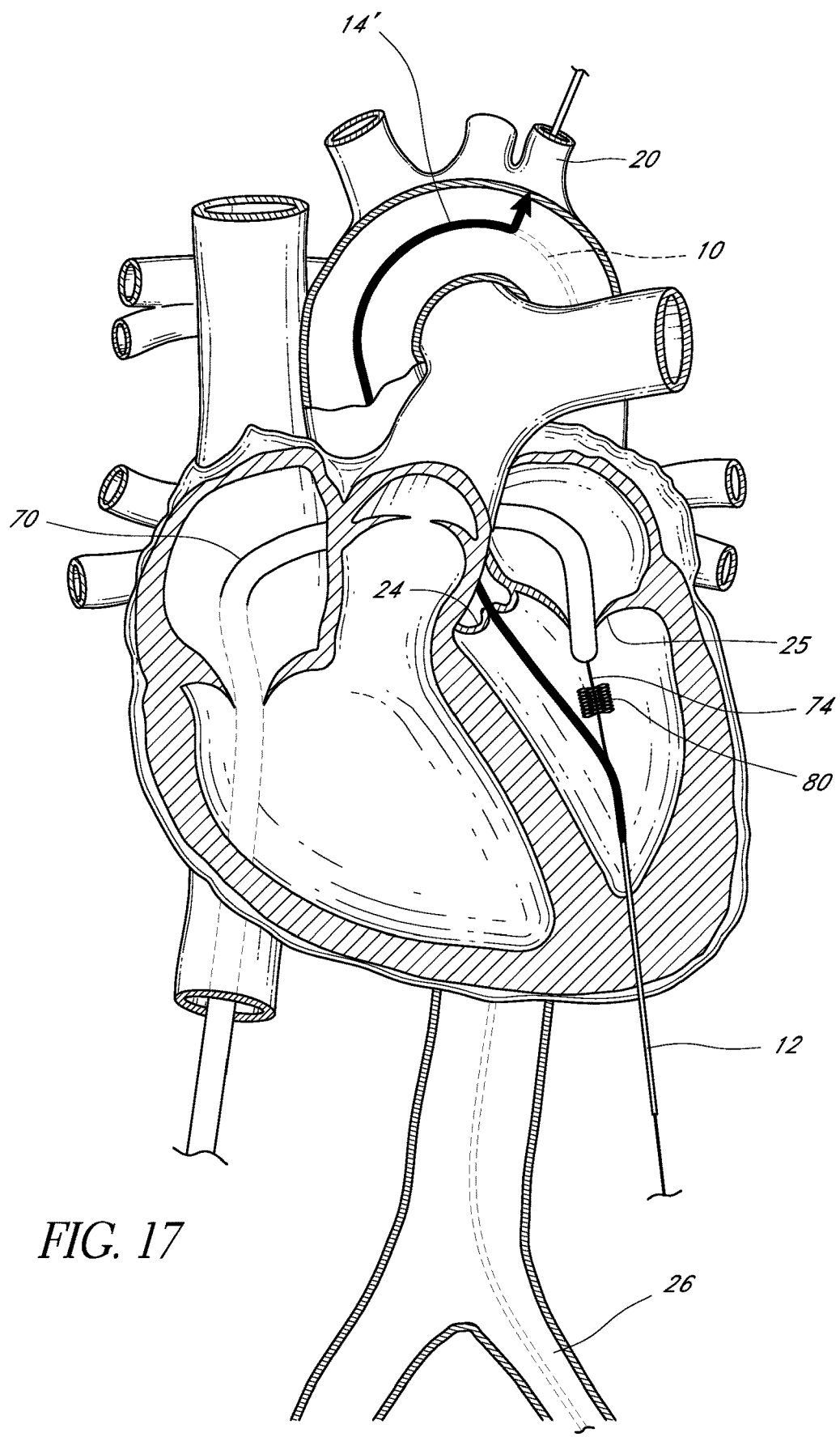
Figure 18:
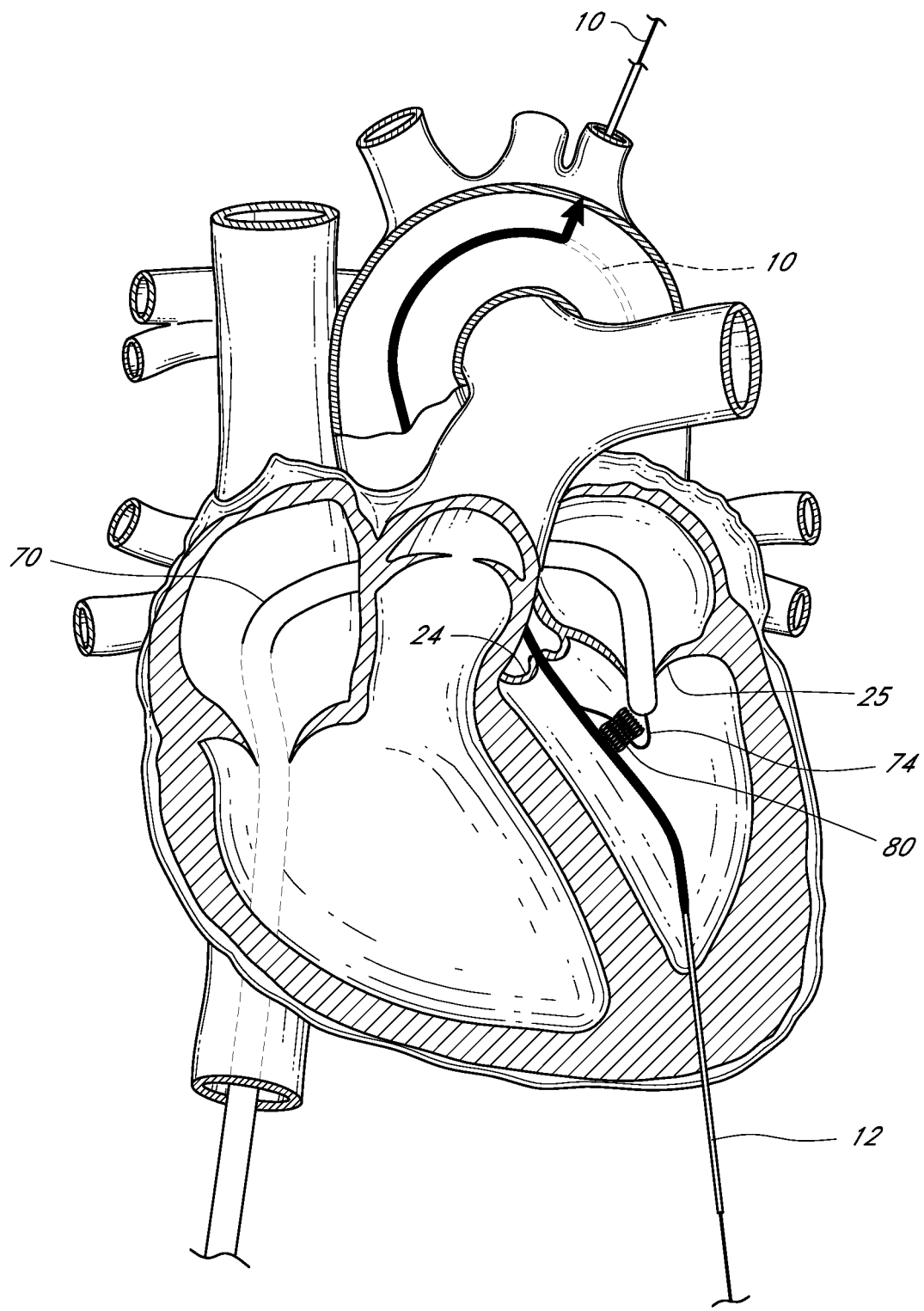
FIGS. 18 and 19 illustrates providing two elongate members that can act as guidewire with independent maneuverability.
Figure 19:
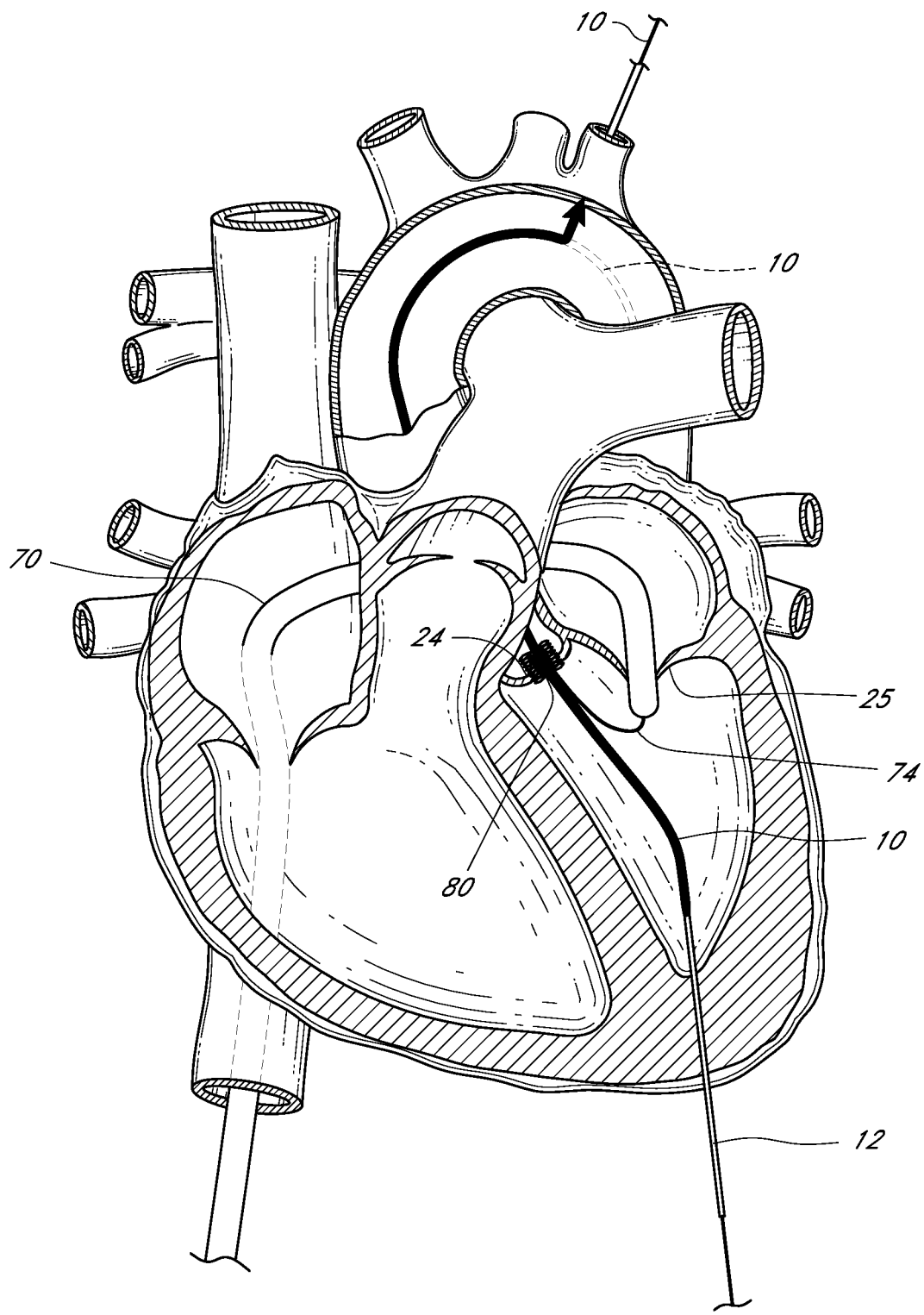

FIGS. 17-19 illustrate treating a condition in the heart and/or arterial vasculature over the venous-arterial rail. The loop 72 of delivery system 70 links to the elongate member 10. In some embodiments, the delivery system 70 links to the elongate member 10 subsequent to the elongate member 10 coupling with the arterial access catheter. In some embodiments, the delivery system 70 links to the elongate member 10 before the elongate member 10 has coupled to the arterial access catheter. In some embodiments, tension in the proximal end of the feed wire 74 is reduced to allow the wire 74 to extend from the delivery system 70 and to track along the elongate member 10 into the arterial vasculature. In the arterial vasculature, the feed wire 74 follows and may in some cases couple with the elongate member 10 along the path 14', as described above. Tension can be applied from outside the cardiac access site to the elongate member 10 to draw the feed wire 74 from the delivery system 70 and into the ventricle 4. Further tension on the elongate member 10 can cause the prosthesis 80 (discussed below) to be drawn out of the delivery system 70. Tension on the elongate member 10 applied at a distal arterial site (e.g., on an externalized distal end of the elongate member 10 after the elongate member 10 has traversed one of the branches of the path 14') can draw the feed wire 74 and/or the prosthesis 80 through the aortic valve 24 and/or to the peripheral artery.

In some embodiments, a prosthesis 80 is delivered to the heart through the delivery system 70. In at least one embodiment, tension is applied through the elongate member 10 from a proximal externalized end of the elongate member 10 in the apical direction to draw the prosthesis 80 from the delivery system 70. After the prosthesis 80 enters the left ventricle 4, tension is applied to the elongate member 10 from a distal externalized end of the elongate member 10 that has been externalized after following a branch of the path 14' to draw the prosthesis 80 into or through the aortic valve 24. Thereafter, the prostheses 80 can be deployed in the aortic valve space or in the vasculature, e.g., in the ascending aorta. In some embodiments, the prosthesis 80 is deployed in the aortic valve annulus. In FIG. 19, the feed wire 74 extends through the lumen of the prosthesis 80, while the elongate member 10 is outside the lumen of the prosthesis 80. In some embodiments, the prosthesis 80 is positioned at the aortic valve 24 and held in place while the elongate member 10 is withdrawn from the aortic valve 24. In some embodiments, the prosthesis 80 is held in place by partially deploying the prosthesis 80. The prosthesis 80 can be self-expandable such that withdrawal of a sheath permits a portion or all of the prosthesis 80 to expand. The prosthesis 80 can be secured to the elongate member 10 while a sheath retaining the prosthesis 80 in a low-profile configuration is withdrawn. As the sheath is withdrawn, the prosthesis 80 is permitted to expand and does expand by virtue of an elastic or shape memory material or member forming a part thereof. The prosthesis 80 could be mounted on a balloon or other expandable member capable of deploying the prostheses 80. In some embodiments, the elongate member 10 is withdrawn from the aortic valve 24 by drawing the elongate member 10 toward the peripheral arterial access site along one of the branches of the path 14' e.g., by pulling on the distal externalized end. In some embodiments, the elongate member 10 is withdrawn from the aortic valve 24 by disengaging the elongate member 10 from the feed wire 74 and pulling on the proximal externalized end of the elongate member 10 and in the apical direction.

In some embodiments, an over-the-wire catheter is used to move the prosthesis 80 along the venous-to-apex rail, along the apex-to-arterial rail, or along the venous-to-arterial rail. The rail can be pulled tight to straighten the rail in certain segments, e.g., from the heart apex through the aortic valve or through the mitral valve. In some embodiments, the prosthesis 80 is coupled to the feed wire 74 and pulled along with the rail. The prosthesis 80 may be coupled to the feed wire 74 by a variety of methods including releasably attaching or crimping onto the feed wire 74 a retaining platform (not shown) that temporarily holds the prosthesis 80 in an undeployed configuration. In other words, systems and method disclosed herein can have a first configuration or mode where a rail can be held stationary, while permitting a catheter or other device that may carry the prosthesis 80 to move relative to the rail such that the catheter, device or prosthesis can be advanced or retracted over the rail. The systems and method herein can have a second configuration or mode where the rail can be coupled to a catheter, device or prosthesis for no relative movement between the rail and the catheter, device or prosthesis such that the rail can be moved through the patient carrying the catheter, component and/or prosthesis. The first configuration can provide a direct push-pull mode. The second configuration can provide an indirect push-pull mode. The second configuration also enable the catheter, device or prosthesis to be pulled from distal a target site or proximal of a target site.

The prosthesis 80 may also be introduced to the heart using methods such as those described in International Application Number PCT/US2014/041366, which is incorporated herein by reference.

Although the present invention has been disclosed with reference to certain specific embodiments of devices and methods, the inventors contemplate that the invention more broadly relates to methods disclosed above, such as those useful for orienting a catheter with respect to an anatomical structure, as well as performing diagnostic and/or therapeutic procedures in the heart or adjacent the heart. For instance, one could place a treatment device, including a stent-graft, in the ascending aorta, the aortic root, the descending aorta, or the abdominal aorta. Accordingly, the present invention is not intended to be limited to the specific structures and steps disclosed herein, but rather by the full scope of the attached claims.

What is claimed is:

1. A method of accessing a heart of a patient, comprising:
   establishing a cardiac access channel through an apical wall of the heart to provide direct access through the apical wall to the left ventricle;
   establishing a vascular access channel through the skin to a peripheral artery;
   advancing a first end of an elongate member from the outside of the apical wall through the cardiac access channel and into the left ventricle, a second end disposed opposite the first end remaining outside the patient;
   drawing the elongate member into and through the vascular access channel to externalize the first end of the elongate member outside of the peripheral artery while leaving the second end outside the apical wall of the heart;
   advancing a venous access catheter from a peripheral venous site through an intra-atrial septum and into a left atrium; and
   snaring the elongate member with a snare that extends from the venous access catheter.

2. The method of claim 1, wherein establishing the cardiac access channel comprises placing an introducer sheath through the heart wall, the introducer sheath comprising a lumen and having an outer profile less than 5 French.

3. The method of claim 2, further comprising removing the elongate member and the introducer sheath; and dosing the cardiac access channel.

4. The method of claim 3, wherein closing the cardiac access channel further comprises applying a biological glue in or adjacent to the cardiac access channel.

5. The method of claim 4, further comprising advancing a balloon catheter to the epicardium and delivering the biological glue through the balloon directly onto the epicardium.

6. The method of claim 3, wherein closing the cardiac access channel further comprises suturing the myocardium to compress the tissue around the cardiac access channel.

7. The method of claim 3, wherein closing the cardiac access channel further comprises delivering a compression member to the epicardium to apply pressure to the tissue at or around the apical wall.

8. The method of claim 1, further comprising:
   advancing an arterial-side snare into the vasculature through the peripheral artery; and
   drawing the elongate member through the peripheral artery using the arterial-side snare to externalize the first end of the elongate member.

9. The method of claim 8, further comprising:
   tensioning the elongate member to establish a delivery platform between a distal portion of the venous access catheter and the cardiac access channel.

10. The method of claim 9, further comprising delivering a prosthetic mitral valve at a level of a mitral valve annulus along the delivery platform after tensioning the elongate member.

11. A method of accessing a heart of a patient, comprising:
    establishing a cardiac access channel through an apical wall of the heart to provide direct access through the apical wall to a left ventricle;
    advancing a first end of a elongate member through the cardiac access channel and into the left ventricle, wherein a second end of the elongate member remains outside the patient;
    advancing a distal end portion of a venous access catheter from a peripheral venous access site across an intra-atrial septum and into a left atrium;
    drawing the first end of the elongate member into and through the venous access catheter to externalize the first end through the peripheral venous access site; and
    drawing a prosthesis from the venous access catheter by applying tension to the elongate member.

12. The method of claim 11, further comprising:
    tensioning the elongate member between the distal end portion and the cardiac access channel.

13. The method of claim 11, wherein the elongate member passes through a lumen of the prosthesis.

14. The method of claim 11, further comprising:
    deploying the prosthesis at the level of the mitral valve annulus.

15. A method of accessing a heart of a patient, comprising:
    establishing a cardiac access channel through an apical wall of the heart to provide direct access through the apical wall to a left ventricle;
    advancing a first end of a elongate member through the cardiac access channel and into the left ventricle, wherein a second end of the elongate member remains outside the patient;
    advancing a distal end portion of a venous access catheter from a peripheral venous access site across an intra-atrial septum and into a left atrium;
    drawing the first end of the elongate member into and through the venous access catheter to externalize the first end through the peripheral venous access site;
    advancing a second catheter over the elongate member from the peripheral venous access site into the left atrium; and
    drawing a prosthesis from the second catheter by applying tension to the elongate member.

* * * * *